(12) United States Patent
Lang

(10) Patent No.: US 6,547,822 B1
(45) Date of Patent: Apr. 15, 2003

(54) OPTHALMIC LENS SYSTEMS

(75) Inventor: Alan J. Lang, Long Beach, CA (US)

(73) Assignee: Advanced Medical Optics, Inc., Santa Ana, CA (US)

(*) Notice: Subject to any disclaimer, the term of this patent is extended or adjusted under 35 U.S.C. 154(b) by 0 days.

(21) Appl. No.: 09/564,317

(22) Filed: May 3, 2000

(51) Int. Cl.⁷ .................................................. A61F 2/16
(52) U.S. Cl. ..................... 623/6.28; 623/6.24; 623/6.54
(58) Field of Search .............................. 623/6.19, 6.11, 623/6.24, 6.28, 6.32

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |

(List continued on next page.)

FOREIGN PATENT DOCUMENTS

| | | |
|---|---|---|
| AU | 3225789 | 10/1989 |
| DE | 2702117 | 7/1978 |
| DE | 3246306 | 6/1984 |
| EP | 939016 | 10/1963 |
| EP | 0246216 | 11/1987 |
| EP | 0342895 | 11/1989 |
| EP | 0351471 | 1/1990 |
| EP | 0566170 | 10/1993 |
| EP | 0691109 | 1/1996 |
| GB | 2129155 | 5/1984 |
| GB | 2146791 | 4/1985 |
| GB | 2192291 | 1/1988 |

(List continued on next page.)

OTHER PUBLICATIONS

IOL Technologie Brochure, MF4 The Autofocus Lens, 1995.
Jacobi, MD., Et Al, Arch Ophthalmol, vol. 117, pp. 17–23, Jan., 1999.
Menezo, Et Al. J Cataract Refract Surg 24, Aug. 1998.
Fechner, Et Al. J Cataract Refract Surg 24, Jan. 1998.
World Optics Inc. Ophthalmology Times, Mar. 15, 1995.
Lolab Corp, Ophthalmology Times, Mar. 15, 1995.
Universe IOL Center, Ocular Surgery News Int'l, No Date Given.
Hanita Lenses, Ocular Surgery News Int'l, No Date Given.
Alcon Surgical, Alcon Laboratories, No Date Given.
Mediphacos LTDA. Ocular Surgery News, Int'l, No Date Given.
Storz Ophthalmics, Inc. Model L122UV ACL, No Date Given.
Opthalmed Inc. OMAC–260, No Date Given.
Chauvin–Opsia, Azurite ACL (0459) No Date Given.
AMO Specs, Model AC–21B, 1992.
Chiron, Clemente Optifit Modell SPSP525 Brochure Translation, Dec. 1998.
Chrion Vision, Nuvita MA20, 1997.

*Primary Examiner*—Corrine McDermott
*Assistant Examiner*—Hieu Phan
(74) *Attorney, Agent, or Firm*—Stout, Uxa, Buyan & Mullins, LLP; Frank J. Uxa; Peter Jon Gluck

(57) ABSTRACT

An ophthalmic lens system for improving the vision of a patient including first and second ophthalmic lenses. Each of these lenses is adapted for implantation in an eye or to be disposed on or in the cornea. The first ophthalmic lens is biased for distance vision and the second ophthalmic lens is biased for intermediate vision. The ophthalmic lenses may be intraocular lenses which are implanted in the eyes of a patient without removal of the natural lens.

42 Claims, 4 Drawing Sheets

U.S. PATENT DOCUMENTS

| | | |
|---|---|---|
| 3,693,301 A | 9/1972 | Lemaitre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Neilsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,704,016 A | 11/1987 | De Carle |
| 4,720,286 A | 1/1988 | Bailey et al. |
| 4,752,123 A | 6/1988 | Blaker |
| 4,759,762 A | 7/1988 | Grendahl |
| 4,769,033 A | 9/1988 | Nordan |
| 4,813,955 A | 3/1989 | Achatz et al. |
| 4,830,481 A | 5/1989 | Futhey et al. |
| 4,881,804 A | 11/1989 | Cohen |
| 4,890,912 A | 1/1990 | Visser |
| 4,890,913 A | 1/1990 | De Carle |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,938,583 A | 7/1990 | Miller |
| 4,955,902 A | 9/1990 | Kelman |
| 4,976,534 A | 12/1990 | Miege et al. |
| 4,990,159 A | 2/1991 | Kraff |
| 5,002,382 A * | 3/1991 | Seidner ............... 351/161 |
| 5,019,098 A * | 5/1991 | Mercier .................. 623/6 |
| 5,019,099 A | 5/1991 | Nordan |
| 5,047,052 A | 9/1991 | Dubroff |
| 5,071,432 A | 12/1991 | Baikoff |
| 5,074,877 A * | 12/1991 | Nordan .................. 623/6 |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,235,452 A * | 8/1993 | Nordan .................. 623/6 |
| 5,258,025 A | 11/1993 | Fedorov et al. |
| 5,260,727 A | 11/1993 | Oksman et al. |
| 5,270,744 A | 12/1993 | Portney |
| 5,476,514 A | 12/1995 | Cumming |
| 5,480,428 A | 1/1996 | Fedorov et al. |
| 5,496,366 A | 3/1996 | Cumming |
| 5,521,656 A | 5/1996 | Portney |
| 5,562,731 A | 10/1996 | Cumming |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,702,440 A | 12/1997 | Portney |
| 5,766,244 A | 6/1998 | Binder |
| 5,776,191 A | 7/1998 | Mazzocco |
| 5,929,969 A | 7/1999 | Roffman |
| 6,231,603 B1 * | 5/2001 | Lang et al. ............ 623/6.37 |

FOREIGN PATENT DOCUMENTS

| | | |
|---|---|---|
| IL | 2058391 | 4/1981 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9712272 | 4/1997 |
| WO | 9821621 | 5/1998 |
| WO | 0066039 | 11/2000 |

* cited by examiner

OPTHALMIC LENS SYSTEMS

BACKGROUND OF THE INVENTION

This invention relates to an ophthalmic lens system which comprises ophthalmic lenses. The ophthalmic lenses may be adapted for implantation in an eye such as intraocular lenses(IOLS) or adapted to be disposed on or in the cornea such as contact lenses or corneal inlays.

When functioning normally, the natural lens of the eye is somewhat elastic and therefore enables good vision of objects at all distances. This accommodation of the natural lens tends to deteriorate with age such that the ability to see well at all distances is lost and eventually the natural lens becomes basically monofocal.

Likewise, when the natural lens is removed as a result of disease or injury and replaced with an IOL, the natural ability of the eye to accommodate is lost completely. However, an ability to have adequate vision at different distances without using spectacles can be provided by the IOL which is implanted following removal of the natural lens. To this end, the IOL may be multifocal as shown and described, for example, in Portney U.S. Pat. No. 5,225,858, Roffman et al U.S. Pat. No. 5,448,312 or Menezes et al U.S. Pat. No. 5,682,223. Alternatively, the IOL may be of the type which is accommodating in that it can be moved by the eye itself, or monofocal with a depth of focus feature as shown and described in Portney U.S. Pat. No. 5,864,378.

Another approach to overcoming loss of accommodation is to use ophthalmic lenses, such as contact lenses or IOLS, with different optical characteristics for each eye. For example with a system known as monovision one lens has a distance vision correction power and the other lens has a near vision correction power. Another example is shown and described in Roffman et al U.S. Pat. No. 5,485,228. It is also known to implant a distant dominant multifocal IOL in one eye and a near dominant multifocal IOL in the other eye as disclosed in the January 1999 issue of Clinical Sciences by Jacobi et al entitled "Bilateral Implantation of Asymmetrical Diffractive Multifocal Intraocular Lenses," pages 17–23.

Ophthalmic multifocal lenses can also be provided with some depth of focus. This is shown and described, for example, in Portney U.S. Pat. No. 5,225,858 and Roffman et al U.S. Pat. No. 5,684,560.

Whether monovision or multifocal ophthalmic lenses are employed, nighttime images may not be the same for both eyes and/or possess halos as when the headlights of an oncoming vehicle are observed. This can significantly reduce the ability of the observer to identify and locate objects near the headlights. For example, halos tend to be created when the patient views a distant object through the near vision portion of the lens, and the greater the add power, the more perceptible is the halo.

For example, this is shown and described in commonly assigned application Ser. No. 09/302,977 filed on Apr. 30, 1999. This application discloses a reduced add power multifocal IOL which reduces the effects of halos. This reduced add power IOL is implanted in a phakic eye in which the natural lens has lost some degree of accommodation, i.e. in partially presbyopic eyes.

Commonly assigned application Ser. No. (Atty. Docket No.: D-2857) filed concurrently herewith also discloses multifocal reduced add power lenses, such as IOLs, which are asymmetric, i.e. have different optical characteristics. However, one of these lenses has an add power for full near vision.

The disclosure of each of the patent applications and patents identified herein is incorporated in its entirety herein by reference.

SUMMARY OF THE INVENTION

This invention provides an ophthalmic lens system which improves the ability of the observer to identify and locate objects at near. The invention also significantly reduces nighttime visual phenomena associated with receiving out of focus simultaneous images from multifocal IOLS and obtains other important advantages.

The ophthalmic lens system of this invention may include first and second lenses for use with first and second eyes of a patient, respectively. Each of the first and second lenses has more than one vision correction power and is therefore multifocal. Although this invention is particularly adapted for IOLS, it is also applicable to lenses which can be disposed on or in the cornea such as contact lenses and corneal inlays.

The first lens is biased for distance vision or distance biased. This may be accomplished, for example, by configuring the first lens so that the best visual acuity provided by the lens is for distant objects, for example, objects at infinity. The first lens provides better visual acuity for objects at infinity than the second lens. Preferably, the first lens substantially optimizes visual acuity from distance to intermediate distances. The first lens has a power including a power required for distance vision correction for the patient. The second lens has a power including a power required for intermediate vision correction for the patient. The second lens preferably is intermediate biased. This may be accomplished, for example, by configuring the second lens so that the best visual acuity provided by the second lens is for objects at intermediate distances. Alternatively, or in addition thereto, the second lens provides better visual acuity from intermediate to near distances than the first lens. Preferably, the second lens enhances visual acuity from intermediate to near distances. In addition to the advantages noted above, this enhanced visual acuity of the second lens significantly enhances intermediate vision and provides functional near image quality. It also minimizes potential undesirable effects by using only a low level of image quality disparity between the images received by the two eyes.

The lenses can be made to have the relatively larger ranges of vision in various ways. For example, this can be accomplished by appropriately splitting the light between distance and intermediate. Thus, the second lens may focus sufficient light to an intermediate focus region so as to contribute to the second lens providing enhanced vision from intermediate to near distances.

Alternatively or in addition thereto, the depth of focus of the zone or zones of the lens which provide intermediate vision correction may be appropriately increased to make the second lens have enhanced vision from intermediate to near distances. This may be accomplished, for example, by controlling the aspheric surface design of the lenses. More specifically, the second lens may have a zone with an add power for intermediate vision correction with such zone having optical aberrations which increase the depth of focus of such zone. In one preferred embodiment, such zone extends radially outwardly and has progressively increasing add powers as the zone extends radially outwardly.

The add power of the lenses is reduced over what it would be if one or both of the lenses had the full or even nearly full add power required for near vision correction. The full add power for near vision correction can range from greater than about 1.75 diopters of add power, and is typically between about 2.0 diopters or about 2.5 diopters to about 3.0 or more diopters of add power. The reduced add power significantly reduces halos. Moreover, when the invention is embodied in an IOL which is implanted in a phakic eye with some accommodation, the near visual quality is even better.

In the interest of keeping the add power low while providing adequate vision quality, preferably the maximum add power of either or both of the first and second lenses is less than the add power required for complete or full near vision correction. Still more preferably, the maximum power of any region of either or both of the first and second lenses is no greater than about the power required for intermediate vision correction. By way of example, the maximum add power for both the first and second lenses may be from about 0.5 diopter to about 1.75 diopters and is preferably from about 1 diopter to about 1.5 diopters. The complete near vision correction is typically between 2.5 and 3.0 diopters of add power. All of the add powers set forth herein are in the spectacle plane.

The first and second lenses are adapted to provide some depth of focus. The first lens provides some depth of focus toward intermediate vision correction and preferably the second lens also provides some depth of focus from far vision correction toward intermediate vision correction.

Each of the first and second lenses has an optical axis. Preferably the power of the first lens is different at a plurality of locations radially outwardly of the optical axis of the first lens, and the power of the second lens is different at a plurality of locations radially outwardly of the optical axis of the second lens.

Viewed from a different perspective, the power of each of the first and second lenses changes along a power curve, for example, in a radially outward direction from the associated optical axis. The power curve for the first lens is different from the power curve for the second lens. The power curve of the first lens may at least contribute to the first lens having good visual acuity from distance to intermediate distances and the power curve of the second lens may at least contribute to the second lens having good visual acuity from intermediate to near distances. Each of the first and second lenses may have a power which varies from about the power required for far vision correction to about a power required for intermediate vision correction. In one embodiment, the first lens has a larger range of vision for distance to intermediate distances than the second lens. In the same or a different embodiment, the second lens has a larger range of vision for intermediate to near distances than the first lens.

In one preferred embodiment, the first lens has first, second and third optical zones arranged radially with respect to the optical axis of the first lens with the second zone being intermediate or between the first and third zones and having a greater add power than either of the first and third zones. Similarly, the second lens has first, second and third optical zones arranged radially with respect to the optical axis of the second lens with the second zone being intermediate the first and third zones and having a greater add power than either of the first and third zones of the second lens.

Although the zones can be of various configurations, they are preferably substantially annular and substantially concentric. Preferably, there are at least two zones. Still more preferably, there are three or five of the zones with the innermost and outermost of the zones having a power for far vision correction.

The power in a radial direction can change either gradually or abruptly. The maximum power in each of the second zones may be substantially the same. In one form of the invention, each of the second zones has a power which is substantially constant, and the area, for example, the annular area, of the second zone of the second lens is larger than the area of the second zone of the first lens. This also contributes to the second lens having better visual acuity from intermediate to near than the first lens.

Although IOLS constructed in accordance with this invention may be implanted following removal of the natural lenses, they are particularly adapted for implantation in phakic eyes having some residual accommodation. Even though the lenses of this invention have a reduced add power, the additional optical power provided by the natural lens of the early presbyope allows excellent visual quality from distance through intermediate to near. With the gradual loss of accommodation with age, the image quality at near will decrease but some visual acuity will remain even for the absolute presbyope, i.e. a patient with total loss of accommodation.

According to one aspect of the method of this invention first and second IOLS having different optical characteristics are implanted in the eyes, respectively, of the patient without removing the natural lenses of the patient. Each of the IOLS has a power required for far vision correction and a power required for intermediate vision correction power with the maximum power of each of the first and second IOLS being less than the add power required for near vision correction for the patient.

According to another feature of the method of this invention, first and second ophthalmic lenses are placed on or in the eyes of a patient with the first lens being distance biased and the second lens being intermediate biased. Although the first and second lenses may be contacts or corneal inlays, the features of this invention are particularly adapted for IOLS which can be implanted, respectively, in the eyes of the patient.

The invention, together with additional features and advantages thereof, may best be understood by reference to the following description taken in connection with the accompanying illustrative drawings.

DESCRIPTION OF THE PREFERRED EMBODIMENT

Figure 1:
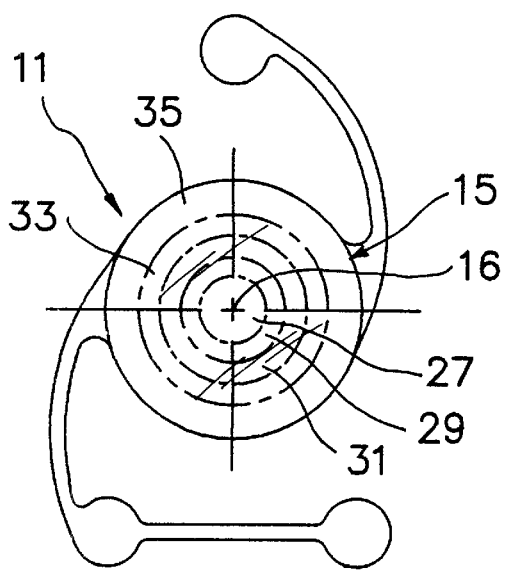
FIG. 1 is a somewhat schematic elevational view of one embodiment of an IOL constructed in accordance with this invention which is substantially optimized for distance-to-intermediate vision.
Figure 2:
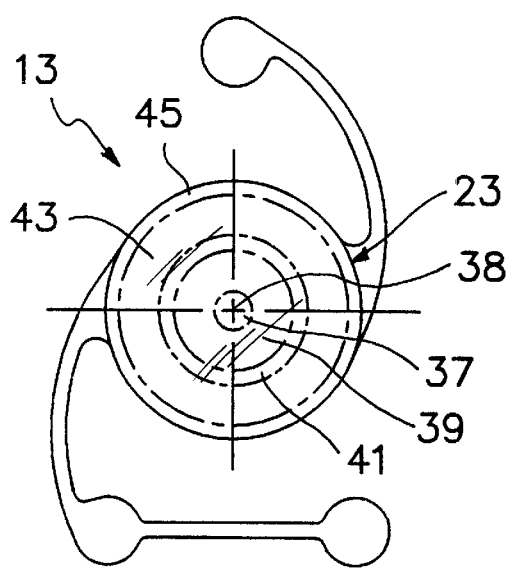
FIG. 2 is a view similar to FIG. 1 of one embodiment of an IOL constructed in accordance with this invention which is enhanced for intermediate to near vision.

FIG. 1 shows an optimized distance-to-intermediate multifocal IOL 11 and FIG. 2 shows an enhanced intermediate-to-near multifocal IOL 13 which together with the IOL 11 form a lens pair or ophthalmic lens system for improving the vision of a patient. The IOL 11 includes a multifocal lens body or optic 15 an optical axis 16 and having powers for a vision correction as described more fully hereinbelow. The IOL 11 also includes generally radially extending footplate-type fixation members 17 which, in this embodiment, are integral with the lens body 15 such that the IOL 11 is one piece.

A variety of configurations can be employed for the fixation members 17 and 18 in order to provide for effective fixation of the IOL 11 in the eye. If the IOL 11 is to be implanted following removal of the natural lens from the eye, then any of those configurations known in the art for that purpose may be employed. On the other hand, if the IOL 11 is to be implanted without removal of the natural lens from the eye, i.e. in an early presbyope, then the fixation members 17 and 18 should be of a configuration and construction which will allow the IOL 11 and the natural lens of the eye to usefully coexist in the eye. In that regard, the configuration shown in FIG. 1 or any of the configurations shown by way of example in commonly assigned application Ser. No. 09/302,977, filed on Apr. 30, 1999 may be employed. The IOL may be fixated to the iris of the eye, may be located in the anterior or posterior chamber of the eye and/or may be fixated at the sulcus of the eye. The fixation members 17 and 18 may be made of materials of construction, such as polymeric materials, for example, acrylic, polypropylene, silicone, polymethylmethacrylate and the like, many of which are conventionally used in fixation members. In the embodiment shown each of the fixation members 17 and 18 has the form shown by way of example in FIGS. 1 and 3, and this adapts the IOL 11 for implantation in the anterior chamber of the eye without removal of the natural lens as shown and described hereinbelow in connection with FIG. 8.

The lens body 15 may be constructed of rigid biocompatible materials such as polymethylmethacrylate (PMMA), or flexible, deformable materials, such as silicone polymeric material, acrylic polymeric material, hydrogel polymeric material and the like, which enable the lens body to be rolled or folded before insertion through a small incision into the eye. Although the lens body 15 shown in FIG. 1 is a refractive lens body, it may be diffractive if desired.

Figure 3:
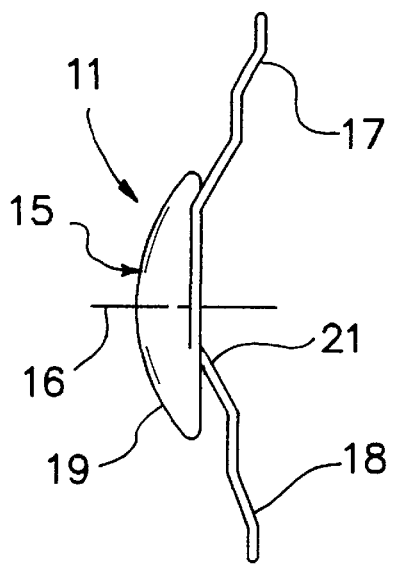
FIG. 3 is a side elevational view of the IOL of FIG. 1.

As shown in FIG. 3, the lens body 15 has a convex anterior surface 19 and a substantially plano posterior surface 21; however, these configurations are merely illustrative. Although the vision correction power may be placed on either of the surfaces 19 or 21, in this embodiment, the anterior surface 19 is appropriately shaped to provide the desired vision correction powers.

The IOL 13 similarly has a multifocal lens body 23 and fixation members 25 and 26 suitably joined to the lens body 23. The optical characteristics of the lens bodies 15 and 23 are different as described more specifically herein below. However, except for the optical characteristics of the lens bodies 15 and 23, the IOLs 11 and 13 may be identical.

With respect to optical characteristics, it can be seen from FIG. 1 that the IOL 11 has a central zone 27 and additional optical zones 29, 31, 33 and 35. In this embodiment, the central zone 27 is circular and the lens body 15 has a circular outer periphery. Also, in this embodiment, the additional optical zones 29, 31, 33 and 35 are annular and concentric with the central zone 27, and all of these zones are centered on the optical axis 16.

Figure 4:
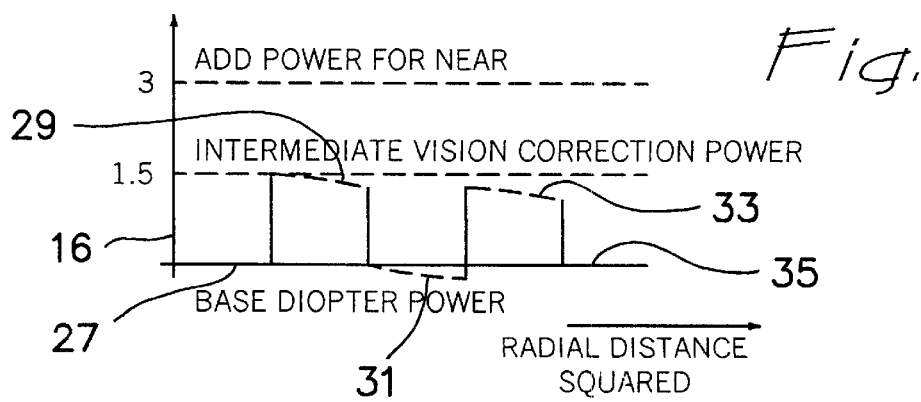
FIG. 4 is a plot of add power of the IOL of FIG. 1 versus radial distance squared from the optical axis of that IOL.
Figure 5:
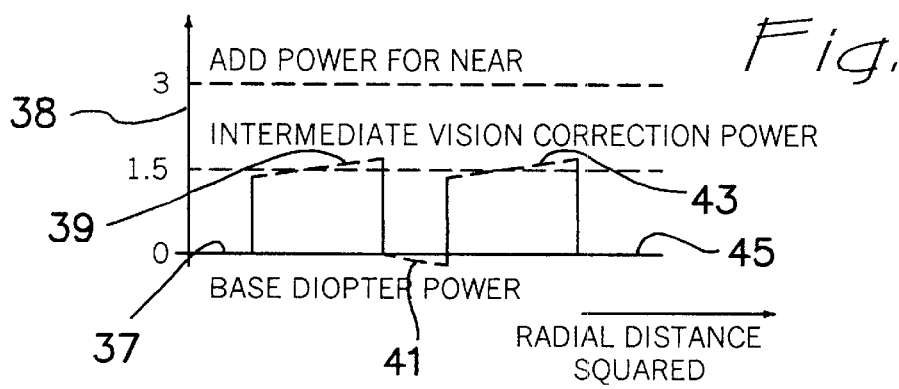
FIG. 5 is a plot similar to FIG. 4 for the IOL of FIG. 2.

With reference to FIG. 4, it can be seen that the central zone 27 and the outermost annular zone 35 have a base diopter power which is the power required by the patient for distance vision correction and is considered as a zero add power. It should also be noted that the diopter power variation shown in FIGS. 4 and 5 is applicable to any point on the surface of the lens bodies 15 and 23, respectively, at a fixed radial distance from the associated optical axes. In other words, the power at any given radial distance from the optical axis 16 is the same, and the power at any given radial distance from the optical axis 38 is the same.

The annular zone 31 has about the power required for distance vision correction. Although the annular zone 31 could have precisely the power required for distance vision correction, i.e. zero add power, in this embodiment, the power of the annular zone 31 decreases progressively and slightly from the outer edge of the zone 29 to about the inner edge of the zone 33 to provide spherical aberration correction. Thus, although the optical power of the zone 31 does diminish in a radial outward direction in this fashion, it nevertheless is considered to be about the power needed for far or distance vision correction for the patient. For example, the vision correction power of the zone 31 may decrease from a zero add power to about 0.25 diopter below the base diopter power.

The zones 29 and 33 have greater vision correction power than the zones 27, 31 and 35 and are preferably at or about the power required for intermediate vision correction. In terms of a single power, the power for intermediate vision correction would be halfway between the base diopter power and the add power for near vision correction. By way of example, if the base diopter power is considered to be zero add power and the add power for near vision correction is considered to be 3 diopters, then the power for intermediate vision correction would be 1.5 diopters of add power. More broadly, however, the intermediate vision correction power may be taken to embrace a zone of from about 0.5 diopter to about 1.75 diopters and preferably that zone may be from about 1 diopter to about 1.5 diopters. When thus considered, the power of the zones 29 and 33 would all be add powers for intermediate vision correction.

The vision correction power in the zone 29 reduces progressively and slightly in a radial outward direction from an add power for intermediate vision correction such as 1.5 diopters as shown in FIG. 4 to a slightly less add power for intermediate vision correction so as to provide for spherical aberration correction. Again, to correct for spherical aberration, the maximum power of the zone 33 is about the minimum power of the zone 29 and reduces progressively and slightly in a radial outward direction as shown in FIG. 4. By way of example, the power of the zone 29 may decrease linearly from about 1.5 diopters to about 1.25 diopters and the vision correction power of the zone 33 may reduce linearly in a radial outward direction from about 1.25 diopters to about 1.0 diopter. Thus, all of the powers of the zones 29 and 33 may be considered as add powers for intermediate vision correction. Thus, it can be readily seen from FIG. 4 that the maximum power of any region of the first lens is no greater than about the power for intermediate vision correction.

The annular areas of the distance correction zones 27, 31 and 35 are intended to be larger than the annular areas of the intermediate power zones 29 and 33. Moreover, there are three of the distance power zones 27 and 35 and only two of the intermediate vision correction zones 29 and 33, although other numbers of these zones may be employed, if desired. Thus, a larger surface of the lens body 15 is dedicated to focusing or directing light to a far focus region than any other focus region. Accordingly, the IOL 11 provides very good visual acuity from distance to intermediate, and provides better visual acuity for objects at infinity than the IOL 13. The IOL 11 is optimized for distance to intermediate vision.

The lens body 23 of the IOL 13 has a circular outer periphery, an optical axis 38, a circular central zone 37 and optical zones 39, 41, 43 and 45 which are preferably annular and concentric with the central zone 37. All of these zones 37, 39, 41, 43 and 45 are centered on the optical axis 38. The nature of the optical zones 37, 39, 41, 43 and 45 makes the lens body 23 optically different from the lens body 15, but except for this the IOLs 11 and 13 may be identical, if desired. It can be seen from FIG. 5 that the central zone 37 and the outer annular zone 45 have the base diopter power, i.e., the power required for distance vision correction for the patient or a zero add power. The intermediate annular zone 41 has about the base diopter power. More specifically, the annular zone 41 has a maximum power which is the base diopter power and the vision correction power of this zone decreases progressively in a radial outward direction to a diopter power which is slightly less than the base diopter power in order to correct for spherical aberrations. By way of example, the minimum power of the zone 41 may be 0.25 diopter below the base diopter power.

The zones 39 and 43 have a vision correction power which is about the add power for intermediate vision correction. In each of the zones 39 and 43, the vision correction power increases progressively in a radial outward direction. For example, the minimum power of each of the zones 39 and 43 may be about 1.25 diopters and the maximum power at the radial outer edge of each of these zones may be about 1.75 diopters.

In this embodiment, the IOL 13 has enhanced intermediate to near vision. In this regard, the intermediate power zones 39 and 43 are provided with optical aberrations which increase the depth of focus of such zone. Specifically, the progressively increasing vision correction powers in a radial outward direction in these zones 39 and 43 increase the spherical aberrations which in turn increases the depth of focus by effectively creating stronger diopter power at radial outward locations in each of these zones to therefore allow closer objects to be in focus. This has the effect of increasing the near visual quality at the expense of the intermediate image quality, thereby raising the overall image quality as described more fully hereinbelow in connection with FIGS. 6A–C and 7A–C. Thus, this increased depth of focus contributes to making the IOL 13 biased or enhanced for intermediate to near vision and certainly more enhanced for intermediate to near vision than the IOL 11 which has spherical aberration correction. Stated differently, the IOL 13 provides better visual acuity from intermediate to near than the IOL 11. Conversely, the IOL 11 is biased or optimized for distance to intermediate vision and certainly provides better visual acuity for distance to intermediate than the IOL 13.

In addition a larger portion of the area of the lens body 23 is used to direct light to an intermediate focus region so as to contribute to the lens body 23 having better visual acuity from intermediate to near than the IOL 11. Thus, the combined areas, that is the combined annular areas, of the zones 39 and 43 are greater than the combined areas of the zones 37, 41 and 45, and this is shown in FIGS. 2 and 5. Consequently, more of the incident light is directed to an intermediate focus region than to a distance or far focus region, and this also contributes to the IOL 13 providing better visual acuity from intermediate to near than the IOL 11 and to providing enhanced intermediate-to-near image quality. As compared with the IOL 11, it can also be seen from FIGS. 4 and 5 that the area of each of the zones 39 and 43 of the IOL 13 is larger than the area of either of the zones 29 and 33 of the IOL 11. This also contributes to the IOL 13 having better visual acuity from intermediate to near than the IOL 11. IOL 13 is intermediate biased, whereas IOL 11 is distance biased.

From FIGS. 4 and 5, it is apparent that the maximum powers of any region of either of the IOLs 11 and 13 are less than the add power required for full near vision correction, the latter being an add power which is at least greater than 1.75 diopters and may be 2.5 or 3.0 diopters. Also, the maximum powers of any region of either of the IOLs 11 and 13 are no greater than about the intermediate vision correction power. The plots of FIGS. 4 and 5 represent power curves showing how the vision correction power of each of the IOLs 11 and 13 changes in a radially outward direction from the optical axes 16 and 38, respectively, and it is apparent that the power curves of FIGS. 4 and 5 are different. Moreover, the differences in these power curves contribute to the range of vision characteristics of IOLs 11 and 13.

FIGS. 1–3 illustrate one way that this invention may be embodied in IOLs. However, the invention may also be embodied in ophthalmic lenses which are adapted to be disposed on or in the cornea such as contact lenses and corneal inlays. The lens bodies 15 and 23 of FIGS. 1 and 2 may also be considered as schematically representing contact lenses or corneal inlays. of course, these latter two forms of ophthalmic lenses do not have the fixation members 17, 18, 25 or 26.

This invention also provides a method of correcting the vision of a patient which comprises placing first and second multifocal ophthalmic lenses on or in the eyes of a patient with the first lens being distance biased and providing better visual acuity for objects at infinity than the second lens. The second lens is intermediate biased and provides better visual acuity from intermediate to near distances than the first lens. The maximum power of the second lens is less than the add power required for near vision correction for the patient. With specific reference to the embodiments shown in FIGS. 1–3, the method includes implanting the IOLs 11 and 13 in the eyes, respectively, of the patient. Although this implantation can follow the removal of the natural lens from the eye, this invention is particularly adapted for carrying out the implantation step without removing the natural lenses of the eyes of the patient so that the patient retains some natural accommodation.

Figure 8:
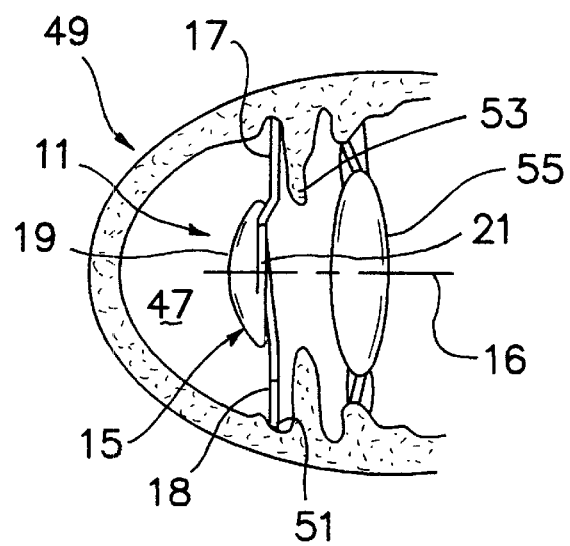
FIG. 8 is a sectional view of an eye with the natural lens in place and the intraocular lens of FIG. 1 implanted in the anterior chamber.

With reference to FIG. 8, the IOL 11 is implanted in an anterior chamber 47 of an eye 49 with the fixation members 17 and 18 in contact with the angle 51 of the iris 53. The eye 49 has a natural lens 55 which has some residual accommodation and which has not been removed. Thus, the IOL 11 is to be used in conjunction with the natural lens 55. The IOL 13, which has optical characteristics different from the IOL 11, is similarly implanted in the other eye of the patient.

Figure 6A:
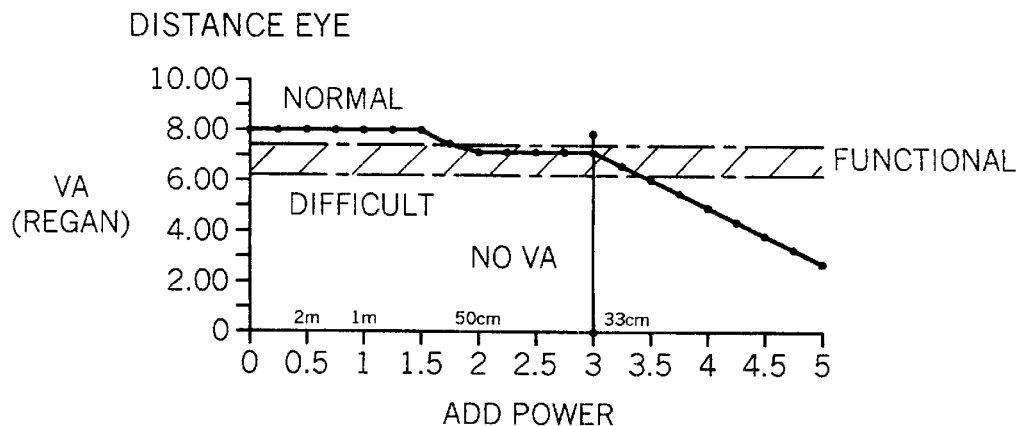
FIG. 6A is a plot of visual acuity versus add power for the IOL of FIG. 1 when implanted in an early presbyope needing 1.5 diopters of add power.
Figure 6B:
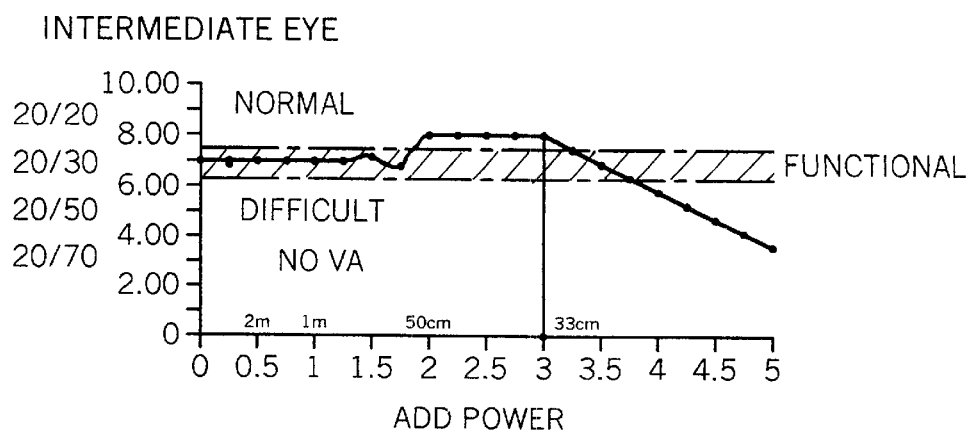
FIG. 6B is a plot similar to FIG. 6A for the IOL of FIG. 2 for the same early presbyope.
Figure 6C:
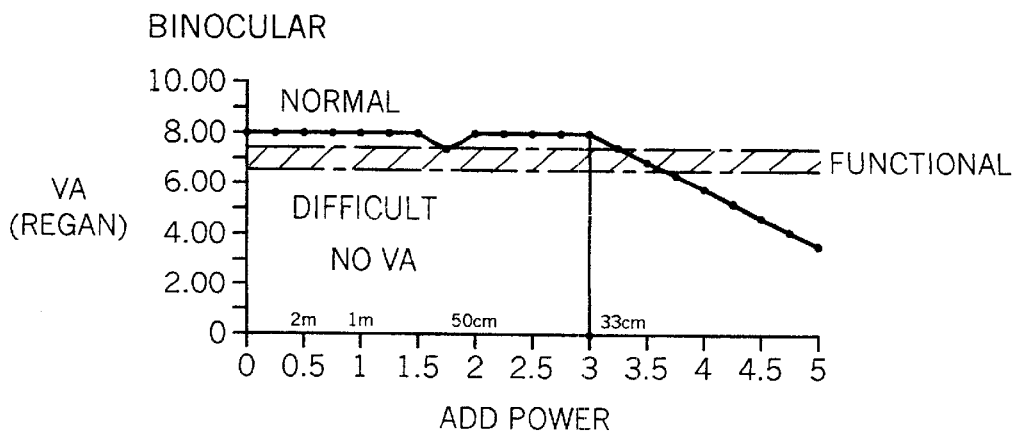
FIG. 6C is a plot similar to FIG. 6A for binocular vision for the same early presbyope.

FIGS. 6A–C are of use in gaining a further understanding of how the IOLs 11 and 13 work in conjunction with the natural lens of the eye. These figures are through-focus-acuity charts for a younger, early presbyope retaining 1.5 diopters of natural accommodation who need 1.5 diopters of add power and has the IOLs 11 and 13 implanted, as shown by way of example in FIG. 8. Each of these figures shows visual acuity (VA) along the ordinate and add power in diopters along the abscissa. In addition, the reciprocal of the diopter add power in meters is also shown along the abscissa. The add power is the add power required by a patient with no accommodation at the corresponding distance indicated on the abscissa. The units for visual acuity or VA are Regan, and in FIG. 6B an approximate correspondence to the 20/x scale is shown. A visual acuity of about 8 corresponds to 20/20 and is considered normal vision. Functional vision is considered to be about 20/30 up to nearly 20/20, and is shown by the cross hatched band in FIGS. 6A–C. Although functional vision is clinically not normal, it may seem normal to the patient. Below about 20/30 vision becomes progressively more difficult and somewhere about 3 Regan or slightly worse than 20/60 there is essentially no usable visual acuity. The visual acuity plots of FIGS. 6A–C and 7A–C are theoretical.

FIG. 6A shows the visual acuity with the distance eye, i.e., the eye in which the optimized distance to intermediate IOL 11 is implanted. In a similar fashion, FIG. 6B shows the visual acuity in the intermediate eye, i.e., the eye in which the enhanced intermediate to near IOL 13 is implanted, and FIG. 6C shows the binocular visual acuity, i.e., the visual acuity for both eyes with the IOLs 11 and 13 implanted. As shown in FIG. 6C, the binocular visual acuity remains normal for the full range from distance to a very close reading distance of 33 centimeters, i.e., zero to 3 diopters of add power.

Because of the reduced add power in both of the IOLs 11 and 13, halos in either eye should be significantly reduced. Also, the between-eye visual acuity difference never exceeds half an acuity line which is approximately 20% of the between-eye visual acuity difference experienced in monovision with a 2.5 diopter add. Thus, the potential for symptoms associated with failure of monovision is significantly reduced.

Figure 7A:
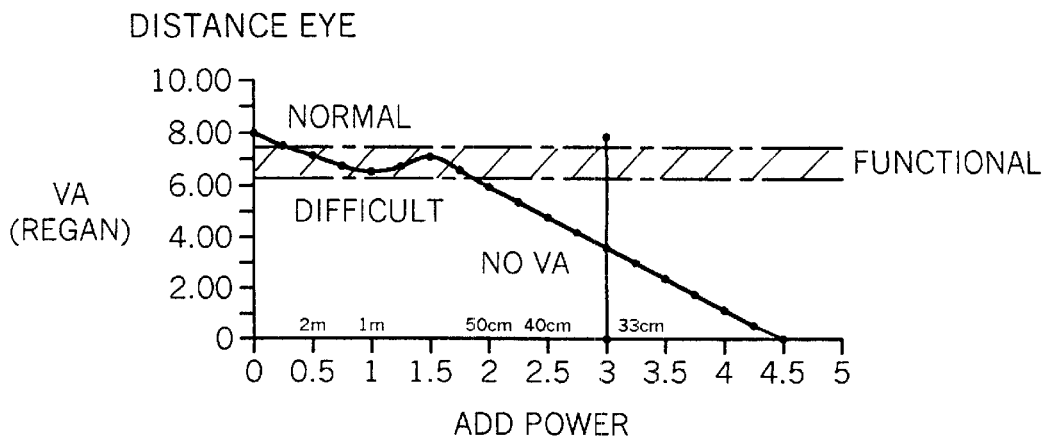
FIGS. 7A, 7B and 7C are plots similar to FIGS. 6A, 6B and 6C, respectively, for the IOLs of FIGS. 1 and 2 implanted in an absolute presbyope.
Figure 7B:
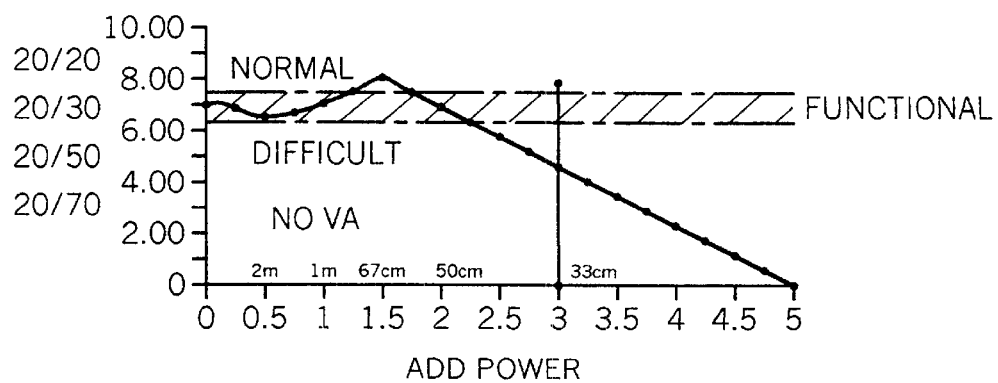
Figure 7C:
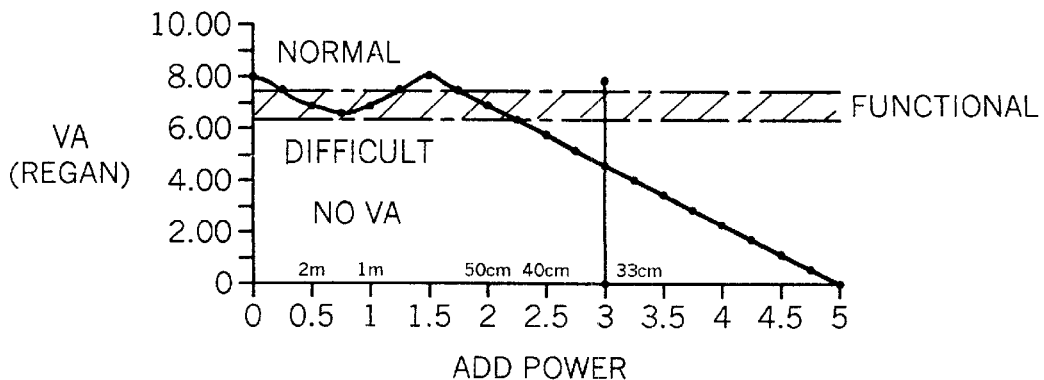

FIGS. 7A–C show the expected-through-focus-acuity for an absolute presbyope with no accommodation using the IOLs 11 and 13. This is equivalent to a pseudophakic patient with these IOLs implanted. The IOL 11 (FIG. 7A) has better visual acuity at infinity than does the IOL 13 (FIG. 7B) as shown by the higher visual acuity at the ordinate. The IOL 11 optimizes visual acuity from distance to intermediate distances as shown by the normal and functional visual acuity (FIG. 7A) from infinity to about 1.75 diopters of add power or about 57 centimeters. By comparing FIG. 7A and 7B, it can be seen that the IOL 13 provides better visual acuity from intermediate to near distances than does IOL 11 and that visual acuity in this range is enhanced. Also, by comparing FIGS. 7A and 7B, it can be seen that the IOL 13 provides better visual acuity for objects at near distances than the IOL 11. FIG. 7B shows that the best visual acuity provided by the IOL 13 is for objects at intermediate distances such as 67 cm which corresponds to 1.5 diopters of add power.

The binocular visual acuity remains functional or better for distance and intermediate objects. However, near reading between 40 centimeters and 33 centimeters becomes difficult. Thus, the absolute presbyope should perform all active tasks well including screening of mail. However, it is likely that about a 1 diopter to 1.5 diopter add power will be needed for extended near work. Nevertheless, the intermediate and near visual acuity for the absolute presbyope is significantly better than the equivalent presbyope without the IOLs 11 and 13 or near vision correction.

It can be seen from FIG. 7B that the intermediate eye has no near vision peak, but only an intermediate peak at about 1.5 diopters or about 67 cm. Accordingly, the only way to increase the near image quality for the absolute presbyope is to increase the depth of focus of the intermediate peak to thereby increase the intermediate to near range of useable image quality.

The depth of focus of the intermediate peak in FIG. 7B can be increased in two ways. First, the shape of the surfaces of the zones 39 and 43 which provide the intermediate vision correction powers can be altered as shown by way of example in FIG. 5 to introduce optical aberrations, e.g., spherical aberrations, which extend the depth of focus but decrease the overall optical quality. However, there is a range of useable optical quality within which there is no impact to clinical vision. For example, many patients can tolerate clinically significant amounts of refractive error, e.g., up to ±1 diopter, without seeking refractive correction.

Secondly, in a simultaneous vision design the visual acuity for intermediate vision can be increased at the expense of distance image quality thereby raising the overall image quality and extending the depth of focus in the useable range of vision. This to some extent counters the decrease in intermediate visual quality associated with an increase in depth of focus by the introduction of optical aberration. The visual acuity for intermediate distances is increased by increasing the amount of light directed to the intermediate zones 39 and 43, as described above in connection with FIG. 5.

Although an exemplary embodiment of the invention has been shown and described, many changes, modifications, and substitutions may be made by one having ordinary skill in the art without necessarily departing from the spirit and scope of this invention.

What is claimed is:

1. An ophthalmic lens system for improving the vision of a patient comprising:

a first multifocal ophthalmic lens for use with one eye of a patient;

a second multifocal ophthalmic lens for use with the other eye of the patient, said second lens having a power including an intermediate add power for intermediate vision correction for the patient and a maximum add power which is less than an add power required for full near vision correction for the patient;

said second lens providing better visual acuity from intermediate to near distances than said first lens; and each of said first and second lenses being adapted for implantation in an eye or to be disposed on or in a cornea of an eye.

2. An ophthalmic lens system as defined in claim 1 wherein the maximum add power of any region of the second lens is no greater than about said intermediate add power.

3. An ophthalmic lens system as defined in claim 1 wherein the maximum add power of any region of the first lens is no greater than about said intermediate add power.

4. An ophthalmic lens system as defined in claim 1 wherein the maximum add powers of any region of the first and second lenses are no greater than about said intermediate add power.

5. An ophthalmic lens system as defined in claim 1 wherein the first lens provides better visual acuity for objects at infinity than the second lens.

6. An ophthalmic lens system as defined in claim 1 wherein the second lens is biased for intermediate vision and the second lens focuses sufficient light to an intermediate focus region so as to contribute to the second lens being intermediate biased.

7. An ophthalmic lens system as defined in claim 1 wherein the second lens has a zone with said intermediate add power and said zone has optical aberrations which increase the depth of focus of said zone.

8. An ophthalmic lens system as defined in claim 7 wherein said zone extends radially outwardly and has progressively increasing powers as said zone extends radially outwardly.

9. An ophthalmic lens system as defined in claim 1 wherein each of the first and second lenses has an optical axis, the power of each of said first and second lenses changes along a power curve in a radially outward direction from the associated optical axis and the power curve for said first lens is different from the power curve for the second lens.

10. An ophthalmic lens system as defined in claim 9 wherein the power curves of the first and second lens at least contribute to the second lens providing better visual acuity from intermediate to near distances than the first lens.

11. An ophthalmic lens system as defined in claim 1 wherein the first and second lenses are intraocular lenses.

12. An ophthalmic lens system as defined in claim 1 wherein the first and second lenses are contact lenses.

13. An ophthalmic lens system as defined in claim 1 wherein the first and second lenses are corneal inlays.

14. An ophthalmic lens system for improving the vision of a patient comprising:
 a first multifocal ophthalmic lens for use with one eye of a patient, said first lens having a power including a power for distance vision correction for the patient;
 a second multifocal ophthalmic lens for use with the other eye of the patient, said second lens having a power including an intermediate add power for intermediate vision correction for the patient and a maximum power which is less than a full add power required for near vision correction for the patient;
 said first lens providing better visual acuity for objects at infinity than the second lens; and
 each of said first and second lenses being adapted for implantation in an eye or to be disposed on or in a cornea of an eye.

15. An ophthalmic lens system as defined in claim 14 wherein the maximum add power of any region of the second lens is no greater than about said intermediate add power.

16. An ophthalmic lens system as defined in claim 14 wherein the maximum add power of any region of the first lens is no greater than about said intermediate add power.

17. An ophthalmic lens system as defined in claim 14 wherein the maximum add powers of any region of the first and second lenses are no greater than about said intermediate add power.

18. An ophthalmic lens system as defined in claim 14 wherein the second lens is biased for intermediate vision correction for the patient.

19. An ophthalmic lens system for improving the vision of a patient comprising:
 a first intraocular lens for use with one eye of the patient said first lens having an optical axis and first, second and third optical zones arranged radially with respect to the optical axis, the second zone being intermediate the first and third zones and having a greater add power than either of the first and third zones;

a second intraocular lens for use with the other eye of the patient said second lens having an optical axis and first, second and third optical zones arranged radially with respect to the optical axis of the second lens, the second zone of the second lens being intermediate the first and third zones of the second lens and having a greater add power than either of the first and third zones of the second lens;
 the maximum add power of any region of the second lens being less than a full add power required for near vision; and
 the first lens providing better visual acuity for objects at infinity than the second lens and the second lens providing better visual acuity from intermediate to near distance than the first lens.

20. An ophthalmic lens system as defined in claim 19 wherein the second and third optical zones of the first lens are substantially annular and substantially concentric.

21. An ophthalmic lens system as defined in claim 19 wherein the first, second and third optical zones of the second lens are substantially annular and substantially concentric.

22. An ophthalmic lens system as defined in claim 19 wherein the best visual acuity provided by the second lens is for objects at intermediate distances.

23. An ophthalmic lens system as defined in claim 19 wherein the second lens is biased for intermediate vision and the second lens directs sufficient light to an intermediate focus region so as to contribute to the second lens being intermediate biased.

24. An ophthalmic lens system as defined in claim 19 wherein the area of said second zone of the second lens is larger than the area of said second zone of the first lens.

25. An ophthalmic lens system as defined in claim 19 wherein said second zone of the second lens extends radially outwardly and has progressively increasing vision correction powers as said zone extends radially outwardly.

26. An ophthalmic lens system for improving the vision of a patient comprising:
 a first multifocal intraocular lens for use with one eye of a patient, said first intraocular lens having a power including a power required for distance vision correction for the patient;
 a second multifocal intraocular lens for use with the other eye of the patient, said second intraocular lens having a power including a maximum power which is less than a full add power required for near vision correction for the patient; and
 the first intraocular lens having better visual acuity for objects at infinity than the second intraocular lens and the second intraocular lens having better intermediate visual acuity for at least some intermediate distances than the first intraocular lens.

27. An ophthalmic lens system as defined in claim 26 wherein the maximum add power of the first intraocular lens is no greater than about the power required for intermediate vision correction.

28. An ophthalmic lens system as defined in claim 26 wherein said maximum power of the second intraocular lens is no greater than about the power required for intermediate vision correction.

29. An ophthalmic lens system as defined in claim 26 wherein the maximum add powers of any region of the first and second intraocular lenses are no greater than for about intermediate vision correction.

30. An ophthalmic lens system comprising:

first and second intraocular lenses for use with first and second eyes of a patient, respectively, each of said first and second lenses having an optical axis;

the power of each of said first and second intraocular lenses changing along a power curve in a radially outward direction from the associated optical axis and the power curve for said first intraocular lens being different from the power curve for the second intraocular lens; and the maximum add power of said first and second intraocular lens being less than an add power required for full near vision correction.

31. An ophthalmic lens system as defined in claim 30 wherein the power of the first intraocular lens varies from about a power required for distance vision correction to said maximum add power which is about a power required for intermediate vision correction.

32. An ophthalmic lens system as defined in claim 30 wherein the best visual acuity provided by the second intraocular lens is for objects at intermediate distances.

33. A method of correcting the vision of a patient comprising:

placing first and second multifocal ophthalmic lenses on or in the eyes of the patient, respectively, with the first lens having better visual acuity for objects at infinity than the second lens, the second lens providing better visual acuity from intermediate to near distances than the first lens and the maximum power of the second lens being less than an add power required for near vision correction.

34. The method of claim 33 wherein the first and second lenses are intraocular lenses and the step of placing includes implanting the first and second lenses in the eyes, respectively, of the patient.

35. The method of claim 34 wherein the step of implanting is carried out without removing the natural lenses of the eyes of the patient whereby the patient retains some accommodation.

36. The method of claim 33 wherein the step of placing includes placing the first and second lenses on or in the corneas, respectively, of the patient.

37. A method of correcting the vision of a patient comprising:

implanting first and second intraocular lenses having different optical characteristics in the eyes, respectively, without removing the natural lenses of the patient with each of said first and second lenses having a power which varies between about a far vision power and about an intermediate vision power and with the maximum power of each of the first and second lenses being less than an add power required for near vision for the patient.

38. A method of correcting the vision of a patient comprising:

placing first and second ophthalmic lenses on or in the eyes of the patient with the first lens being biased for distance vision for the patient and the second lens being biased for intermediate vision.

39. The method of claim 38 wherein the first and second lenses are intraocular lenses and the step of placing includes implanting the first and second lenses in the eyes, respectively, of the patient.

40. The method of claim 39 wherein the step of implanting is carried out without removing the natural lenses of the eyes of the patient whereby the patient retains some accommodation.

41. An ophthalmic lens system for improving the vision of a patient comprising:

a first multifocal ophthalmic lens for use with one eye of a patient, said first lens being biased for distance vision;

a second multifocal ophthalmic lens for use with the other eye of the patient, said second lens being biased for intermediate vision and having a maximum add power which is less than an add power required for full near vision correction for the patient; and each of said first and second lenses being adapted for implantation in an eye or to be disposed on or in the cornea.

42. An ophthalmic lens system as defined in claim 41 wherein each of said lenses is an intraocular lens.

* * * * *